United States Patent
Glazier

(10) Patent No.: US 10,524,909 B2
(45) Date of Patent: Jan. 7, 2020

(54) RETAINING CAGE TO PERMIT RESHEATHING OF A TAVI AORTIC-FIRST TRANSAPICAL SYSTEM

(71) Applicant: St. Jude Medical, Cardiology Division, Inc., St. Paul, MN (US)

(72) Inventor: Valerie J. Glazier, Eden Prairie, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 223 days.

(21) Appl. No.: 13/787,056

(22) Filed: Mar. 6, 2013

(65) Prior Publication Data

US 2014/0107758 A1    Apr. 17, 2014

Related U.S. Application Data

(60) Provisional application No. 61/713,191, filed on Oct. 12, 2012.

(51) Int. Cl.
*A61F 2/24*    (2006.01)
*A61F 2/95*    (2013.01)
(Continued)

(52) U.S. Cl.
CPC ............ *A61F 2/2436* (2013.01); *A61F 2/962* (2013.01); *A61F 2/966* (2013.01); *A61F 2002/9534* (2013.01); *A61F 2002/9665* (2013.01)

(58) Field of Classification Search
CPC .... A61M 3/0291; A61M 29/02; A61M 25/04; A61B 2017/3484; A61B 2017/1205;
(Continued)

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 A1 | 11/2002 |

(Continued)

OTHER PUBLICATIONS

International Search Report and Written Opinion for Application No. PCT/US2013/064072 dated Dec. 6, 2013.
(Continued)

*Primary Examiner* — Katherine H Schwiker
(74) *Attorney, Agent, or Firm* — Lerner, David, Littenberg, Krumholz & Mentlik, LLP

(57) ABSTRACT

A delivery device for an implantable medical device includes an inner shaft extending in a longitudinal direction and an outer shaft surrounding at least a longitudinal portion of the inner shaft. The outer shaft is slidable relative to the inner shaft in the longitudinal direction. A sheath surrounds a longitudinal portion of the outer shaft, the sheath having an outer diameter and being slidable in the longitudinal direction between a first position enclosing the medical device and a second position exposing the medical device to permit full functionality of the medical device. A retaining cage is coupled to the outer shaft, the retaining cage being configured and arrange to collapse the medical device during resheathing.

21 Claims, 7 Drawing Sheets

(51) Int. Cl.
 *A61F 2/966* (2013.01)
 *A61F 2/962* (2013.01)

(58) Field of Classification Search
 CPC .... A61F 2/958; A61F 2/95; A61F 2002/9505;
 A61F 2002/9534; A61F 2/962; A61F
 2/966; A61F 2002/9511; A61F
 2002/9528; A61F 2002/9665; A61F
 2/954; A61F 2/97; A61F 2/2427; A61F
 2/243; A61F 2/2436; A61F 2/2439; A61F
 2002/9522; A61F 2002/011; A61F 2/2433
 USPC ...... 623/1.11, 1.12, 1.19; 606/108–110, 113,
 606/194, 198; 604/104–107
 See application file for complete search history.

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,415,664 A * | 5/1995 | Pinchuk | A61F 2/95 604/523 |
| 5,480,423 A | 1/1996 | Ravenscroft et al. | |
| 5,683,451 A * | 11/1997 | Lenker | A61F 2/07 606/198 |
| 5,702,419 A * | 12/1997 | Berry | A61F 2/91 606/108 |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,329,278 B2 | 2/2008 | Seguin et al. | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| D684,692 S | 6/2013 | Braido | |
| 2002/0036220 A1 | 3/2002 | Gabbay | |
| 2002/0165554 A1* | 11/2002 | Dworschak | A61F 2/95 606/108 |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0015224 A1* | 1/2004 | Armstrong | A61F 2/95 623/1.12 |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0184226 A1 | 8/2006 | Austin | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0239254 A1 | 10/2007 | Chia et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255580 A1* | 10/2008 | Hoffman | A61F 2/95 606/108 |
| 2008/0255662 A1 | 10/2008 | Stacchino et al. | |
| 2008/0262590 A1* | 10/2008 | Murray | A61F 2/95 623/1.11 |
| 2008/0262602 A1 | 10/2008 | Wilk et al. | |

(56) References Cited

U.S. PATENT DOCUMENTS

| | | |
|---|---|---|
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2009/0234428 A1* | 9/2009 | Snow .................. A61F 2/95 623/1.11 |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0178588 A1* | 7/2011 | Haselby .................. A61F 2/915 623/1.11 |
| 2011/0245917 A1 | 10/2011 | Savage et al. |
| 2011/0276121 A1* | 11/2011 | Levine .......................... 623/1.12 |
| 2011/0301702 A1 | 12/2011 | Rust et al. |
| 2012/0310320 A1* | 12/2012 | Gill ........................ A61F 2/966 623/1.11 |

FOREIGN PATENT DOCUMENTS

| | | |
|---|---|---|
| DE | 202008009610 U1 | 12/2008 |
| EP | 0696447 A2 | 2/1996 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008070797 A2 | 6/2008 |
| WO | 2009/042196 A2 | 4/2009 |
| WO | 2010008548 A2 | 1/2010 |
| WO | 2010042950 A2 | 4/2010 |
| WO | 2010096176 A1 | 8/2010 |
| WO | 2010098857 A1 | 9/2010 |

OTHER PUBLICATIONS

Catheter-implanted prosthetic heart valves, Knudsen, L.L., et al., The International Journal of Artificial Organs, vol. 16, No. 5 1993, pp. 253-262.
Design U.S. Appl. No. 29/375,243, filed Sep. 20, 2010.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Percutaneous aortic valve replacement: resection before implantation, 836-840, Quaden, Rene et al., European J. of Cardio-thoracic Surgery, 27 (2005).
Ruiz, Carlos, Overview of PRE-CE Mark Transcatheter Aortic Valve Technologies, Euro PCR (powerpoint)—dated May 25, 2010?
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.

* cited by examiner

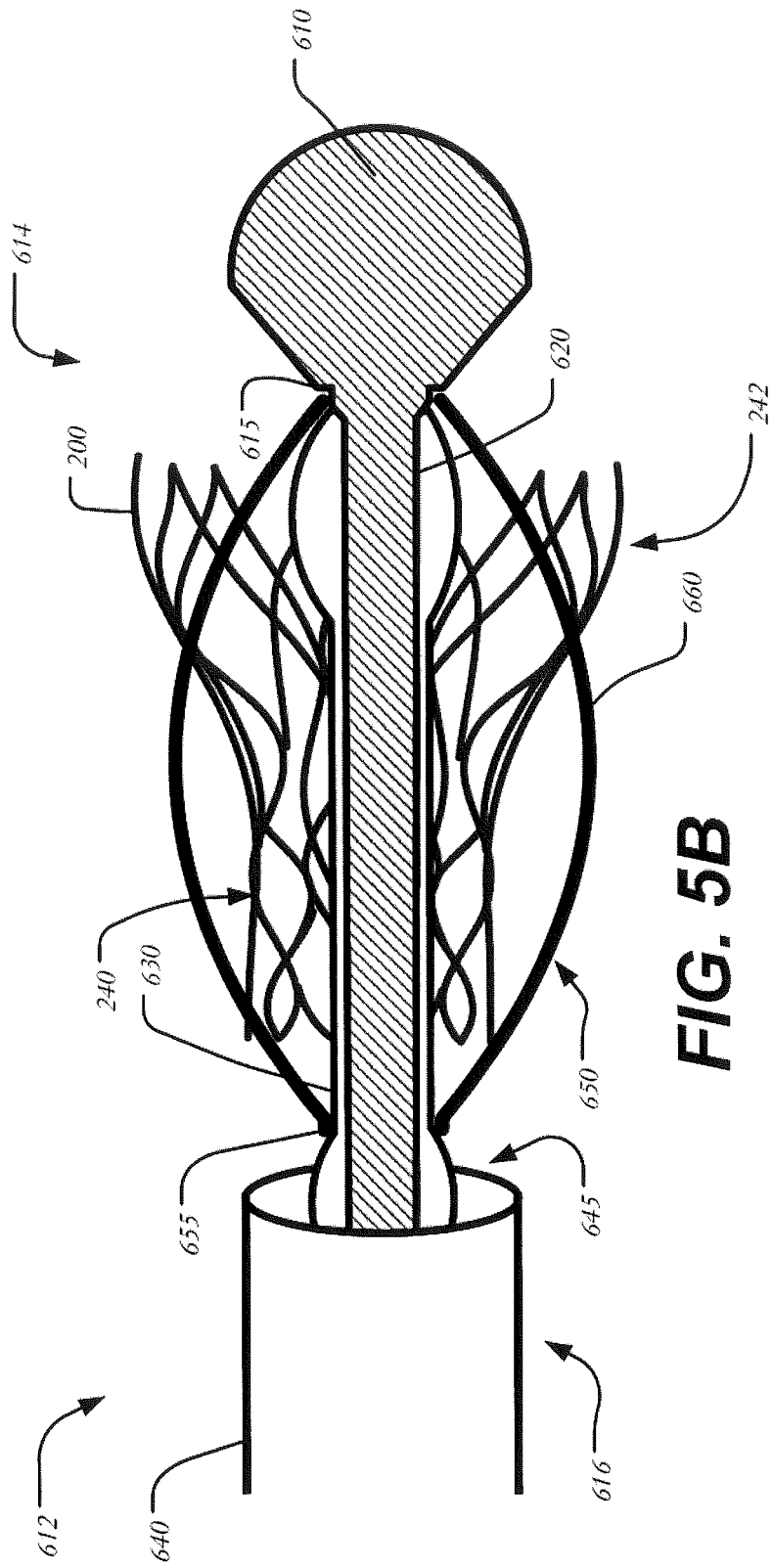

RETAINING CAGE TO PERMIT RESHEATHING OF A TAVI AORTIC-FIRST TRANSAPICAL SYSTEM

CROSS REFERENCE TO RELATED APPLICATION

The application claims the benefit of the filing date of U.S. Provisional Patent Application No. 61/713,191 filed Oct. 12, 2012, the disclosure of which is hereby incorporated herein by reference.

BACKGROUND OF THE INVENTION

The present invention relates to heart valve replacement and, in particular, to collapsible prosthetic heart valves. More particularly, the present invention relates to device and methods for repositioning collapsible prosthetic heart valves during the deployment procedure.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, the annulus end of the valve is typically unsheathed and expanded first, while the aortic end of the valve remains sheathed. Once the valve has expanded, it may be desirable for the valve to be repositioned in the patient's aortic annulus. To accomplish this, a user (such as a surgeon or an interventional cardiologist) may desire the ability to resheath the valve, so that the valve can be repositioned while in a collapsed state. After the valve has been repositioned, the user can again release the valve.

Once a self-expanding valve has been fully deployed, it expands to a diameter larger than that of the sheath that previously contained the valve in the collapsed condition, making resheathing impossible, or difficult at best. Some have attempted to only partially deploy the valve in order to resheath the valve. However, doing so limits the user's ability to test valve function and fitment.

Despite the various improvements that have been made to the collapsible prosthetic heart valve delivery process, conventional delivery devices, systems, and methods suffer from some shortcomings. For example, in conventional delivery devices for self-expanding valves, it is difficult to control how much of the valve remains in the sheath during a partial deployment, and the user may accidentally deploy the valve fully before verifying that the annulus end of the valve is in the optimal position in the patient's valve annulus, thereby taking away the opportunity to resheath and reposition the valve. Moreover, it is not possible at this time using conventional delivery devices to determine whether a valve assembly will function as intended without full deployment of the heart valve. Due to anatomical variations between patients, a fully deployed heart valve may need to be removed from the patient if it appears that the valve is not functioning properly. Removing a fully deployed heart valve increases the length of the procedure and increases the risk of damage to surrounding tissues.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

SUMMARY OF THE INVENTION

In some embodiments, a medical device implantation system includes (a) a shaft extending in longitudinal directions, (b) a medical device including a stent disposed around the shaft, the stent being expandable in radially outward directions transverse to the longitudinal directions, (c) a sheath surrounding the shaft, the sheath being slidable relative to the shaft in a first longitudinal direction from a closed position in which the sheath surrounds the stent to an open position in which the sheath is longitudinally offset from the stent and in a second longitudinal direction from the open position towards the closed position, and (d) a cage including a plurality of fingers, each finger having a first end attached to the shaft and extending in the second longitudinal direction from the first end, each finger having an engagement section extending radially outwardly of the stent over at least a portion of the stent adjacent the first end of the finger when the stent is in a collapsed condition, the engagement section of each finger being movable away from the shaft during expansion of the stent and being movable toward the shaft responsive to movement of the sheath relative to the shaft in the second longitudinal direction so that the stent can be collapsed by moving the sheath in the second longitudinal direction.

In some examples, the shaft may include a trailing end and a leading end, the first longitudinal direction is a rearward direction toward the trailing end of the shaft, and the second longitudinal direction is a forward direction toward the leading end of the shaft. The fingers may have second ends remote from the first ends and wherein the second ends of the fingers are free from the shaft when the stent is in a fully-expanded condition so that when the stent is in the fully-expanded condition and engaged with the body of a subject, the fingers can be disengaged from the stent by retracting the shaft rearwardly relative the body of the subject. The plurality of fingers may be formed of a shape-memory alloy capable of expanding when the sheath is retracted. The plurality of fingers may be formed of nitinol. The plurality of fingers may be interwoven with the medical device when the sheath is in the open position. The plurality of fingers may encapsulate the medical device when the sheath is in the open position.

The system may further include a distal cap movably mounted to the shaft, the distal cap having indentations for receiving the second ends of the plurality of fingers, the plurality of fingers being releasable from the indentations of the distal cap by advancing the distal cap in the second longitudinal direction. The system may further include a handle coupled to the shaft and the sheath, the handle being capable of actuating the shaft and the sheath independently. The medical device may be a prosthetic heart valve. The system may be sized for transapical delivery of a heart valve.

In some embodiments, a medical device implantation system includes (a) a shaft extending in longitudinal directions, (b) a medical device including a stent disposed around the shaft, the stent being expandable in radially outward directions transverse to the longitudinal directions, (c) a sheath surrounding the shaft, the sheath being slidable relative to the shaft in a first longitudinal direction from a closed position in which the sheath surrounds the stent to an open position in which the sheath is longitudinally offset from the stent and in a second longitudinal direction from the open position towards the closed position, and (d) a retaining cage coupled to the shaft, the retaining cage being configured and arrange to collapse the medical device by moving the sheath relative to the shaft in the second longitudinal direction from an open position to a closed position.

In some examples, the shaft has a trailing end and a leading end, the first longitudinal direction is a rearward direction toward the trailing end of the shaft, and the second longitudinal direction is a forward direction toward the leading end of the shaft. The system may be sized for transapical delivery of a heart valve.

In some embodiments, a method of delivering an implantable medical device includes (a) using a delivery system including (i) a shaft extending in first and second longitudinal directions and having radial directions transverse to the longitudinal directions, (ii) a medical device including a stent in a collapsed condition surrounding the shaft, (iii) a cage including longitudinally-extending fingers having first ends attached to the shaft and engagement sections disposed outwardly of the stent and (iv) a sheath in a closed position in which the sheath surrounds the stent and fingers, advancing the system until the device is disposed at a target location in the body of a subject, (b) moving the sheath relative to the shaft in the first longitudinal direction from the closed position to an open position in which the sheath is longitudinally offset from the stent, (c) expanding the stent until the stent is at least partially engaged with the body of the subject, the engagement sections of the fingers being displaced radially outwardly by expansion of the stent and (d) releasing the device from the cage and withdrawing the sheath, shaft and cage from the body of the subject.

In some examples, the method further includes evaluating positioning or functionality of the medical device after the expanding step and prior to releasing the medical device from the cage. The method may further include the step of displacing the engagement sections of the fingers radially inwardly to at least partially collapse the stent. The step of displacing the engagement sections of the fingers radially inwardly may be performed by moving the sheath relative to the shaft in the second longitudinal direction. Releasing the medical device from the cage may include moving the shaft and the fingers in the second longitudinal direction relative to the body of the patient.

In some examples, the medical device is a prosthetic aortic valve the target location is at or adjacent the native aortic valve. The advancing step may be performed by advancing the system through the left ventricle to the target location, and wherein the step of moving the sheath in first longitudinal direction is performed by moving the sheath from the target location toward the left ventricle. In some examples, prior to the expanding step, the fingers may have sections extending through openings in the stent and the step of releasing the medical device from the cage includes untwining the plurality of fingers from the stent. The delivery device may further include a cap and second ends of the plurality of fingers are engaged in the cap prior to the expanding step, the method further comprising releasing the plurality of fingers from the indentations of the distal cap by advancing the cap relative to the shaft and fingers in the second longitudinal direction. The step of expanding the stent may be performed by self-expansion of the stent.

BRIEF DESCRIPTION OF THE DRAWINGS

Various embodiments of the presently disclosed delivery system are disclosed herein with reference to the drawings, wherein:

FIG. 5B is a view of similar to FIG. 5A but depicting the delivery device of FIG. 5A in a partially deployed state;

Various embodiments of the present invention will now be described with reference to the appended drawings. It is appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve into a patient, the terms "trailing" and "leading" are to be taken as relative to the user of the delivery devices. "Trailing" is to be understood as relatively close to the operator, and "leading" is to be understood as relatively farther away from the operator.

Figure 1:
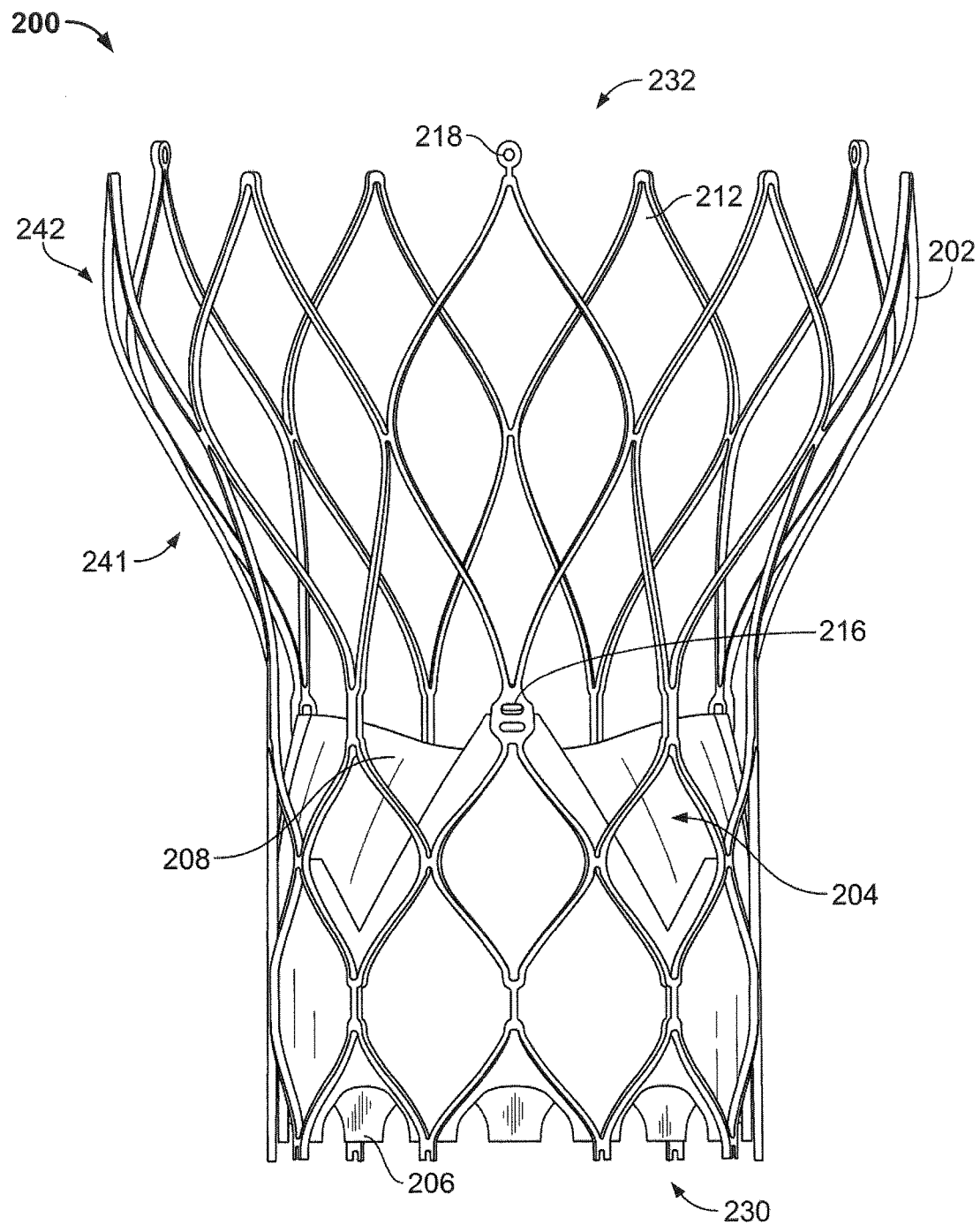
FIG. 1 is a partial side elevational view of a collapsible prosthetic heart valve.

FIG. 1 shows a collapsible prosthetic heart valve 100 according to an embodiment of the present disclosure. The prosthetic heart valve 100 is designed to replace the function of a native aortic valve of a patient. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference Prosthetic heart valve 200 includes an expandable stent 202 which may be formed from biocompatible materials that are capable of self-expansion, such as, for example, shape memory alloys such nitinol. Stent 202 extends from a proximal or annulus end 230 to a distal or aortic end 232, and includes an annulus section 240 adjacent the proximal end and an aortic section 242 adjacent the distal end. The annulus section 240 has a relatively small cross-section in the expanded condition, while the aortic section 242 has a relatively large cross-section in the expanded condition. Preferably, annulus section 240 is in the form of a cylinder having a substantially constant diameter along its length. A transition section 241 tapers outwardly from the annulus section 240 to the aortic section 242. Each of the sections of the stent 202 includes a plurality of cells 212 connected to one another in one or more annular rows around the stent. For example, as shown in FIG. 1, the annulus section 240 may have two annular rows of complete cells 212 and the aortic section 242 and transition section 241 may each have one or more annular rows of partial cells 212. The cells 212 in the aortic section 242 may be larger than the cells 212 in the annulus section 240. The larger cells in the aortic section 242 better enable the prosthetic valve 200 to be positioned without the stent structure interfering with blood flow to the coronary arteries.

Stent 202 may include one or more retaining elements 218 at the distal end 232 thereof, the retaining elements being sized and shaped to cooperate with female retaining structures provided on the deployment device. The engagement of retaining elements 218 with the female retaining structures on the deployment device helps maintain prosthetic heart valve 200 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

The stent 202 may also include a plurality of commissure points 216 for attaching the commissure between two adjacent leaflets to the stent. As can be seen in FIG. 1, the commissure points 216 may lie at the intersection of four cells 212, two of the cells being adjacent one another in the same annular row, and the other two cells being in different annular rows and lying in end-to-end relationship. Preferably, commissure points 216 are positioned entirely within annulus section 240 or at the juncture of annulus section 240 and transition section 241. Commissure points 216 may include one or more eyelets which facilitate the suturing of the leaflet commissure to the stent.

The prosthetic heart valve 200 includes a valve assembly 204 positioned in the annulus section 240. Valve assembly 204 may be secured to stent 202 by suturing from the struts constituting the cells of the stent and/or suturing to the commissure points of the stent. Valve assembly 204 includes a cuff 206 and a plurality of leaflets 208 which collectively function as a one-way valve by contacting one another. FIG. 1 illustrates a prosthetic heart valve for replacing a native tricuspid valve, such as the aortic valve. Accordingly, prosthetic heart valve 200 is shown in FIG. 1 with three leaflets 208, as well as three commissure points 216. However, it will be appreciated that the prosthetic heart valves according to this aspect of the invention may have a greater or lesser number of leaflets and commissure points.

Although cuff 206 is shown in FIG. 1 as being disposed on the lumenal or inner surface of annulus section 240, it is contemplated that the cuff may be disposed on the ablumenal or outer surface of annulus section 240, or may cover all or part of either or both of the lumenal and ablumenal surfaces of annulus section 240. Both the cuff 206 and the leaflets 208 may be wholly or partly formed of any suitable biological material such as bovine or porcine pericardium or polymers, such as PTFE, urethanes and the like.

As is shown in FIG. 1, the entirety of valve assembly 204, including the leaflet commissures, is positioned in the annulus section 240 of stent 202. When opened, the leaflets may extend further into the transition region or may be designed such that they remain substantially completely within the annulus region. That is, in this particular valve substantially the entirety of valve assembly 204 is positioned between the proximal end 230 of stent 202 and the commissure points 216, and none of the valve assembly 204 is positioned between commissure points 216 and the distal end 232 of the stent.

The prosthetic heart valve described above may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device, including the delivery devices described in detail below. During delivery, the prosthetic heart valve is disposed inside the delivery device in the collapsed condition. The delivery device may be introduced into a patient using a transfemoral, transapical or transseptal approach. Once the delivery device has reached the target site, the user may deploy the prosthetic heart valve. Upon deployment, the prosthetic heart valve expands into secure engagement within the native anatomic structure such as the aortic annulus. When the prosthetic heart valve is properly positioned inside the patient, it works as a one-way valve, allowing blood to flow in one direction and preventing blood from flowing in the opposite direction.

In a prosthetic heart valve, the valve assembly may be spaced from the distal or aortic end of the stent by a distance that enables deployment of the heart valve by an amount sufficient for the valve leaflets of the prosthetic valve to operate as intended, while the distal end of the stent remains captured by the delivery device. More particularly, as will be explained further below, the annulus end of the prosthetic heart valve may be deployed first while the aortic end of the prosthetic heart valve remains at least partially covered by the sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve leaflets are properly positioned relative to the native valve annulus, and whether the valve is functioning properly. If the user determines that the positioning and operation of the valve are acceptable, the remainder of the valve may be deployed. However, if it is determined that the leaflet position is improper or that the valve is not functioning properly, the user may resheath the valve and either reposition it for redeployment, or remove it entirely from the patient. This can be particularly important in very high risk patients who would typically be recipients of these types of valves, because of the nature of their condition and the impact that may have on the shape and/or condition of the native valve and valve annulus.

Figure 2:
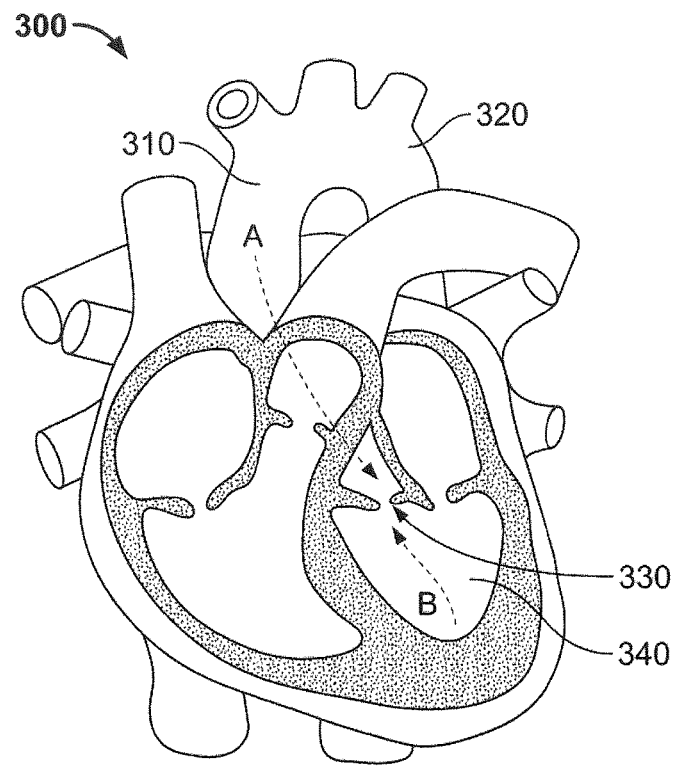
FIG. 2 is a schematic of the heart, showing two approaches for delivering a prosthetic aortic heart valve.

FIG. 2 illustrates a human heart 300 and two varying approaches of delivering a prosthetic heart valve to its intended target at the aortic valve 330. As illustrated in FIG. 2, the heart 300 includes an aorta 310, an aortic arch 320 and a left ventricle 340. Two separate paths are available for introducing a prosthetic heart valve to the aortic valve 330.

A transfemoral approach of the prosthetic heart valve is indicated by the dashed arrow and the letter "A" in FIG. 2. In this method, the prosthetic heart valve is inserted into the femoral artery, tracked throughout the vasculature and then introduced to the target site via the aortic arch 320. Echocardiography and other means may be used to help guide the delivery device through this approach.

A second dashed arrow, labeled as "B" indicates a transapical approach of the prosthetic heart valve. In transapical delivery, a small incision is made between the ribs and into the apex of the left ventricle 340 to deliver the prosthetic heart valve to the target site.

Figure 3:
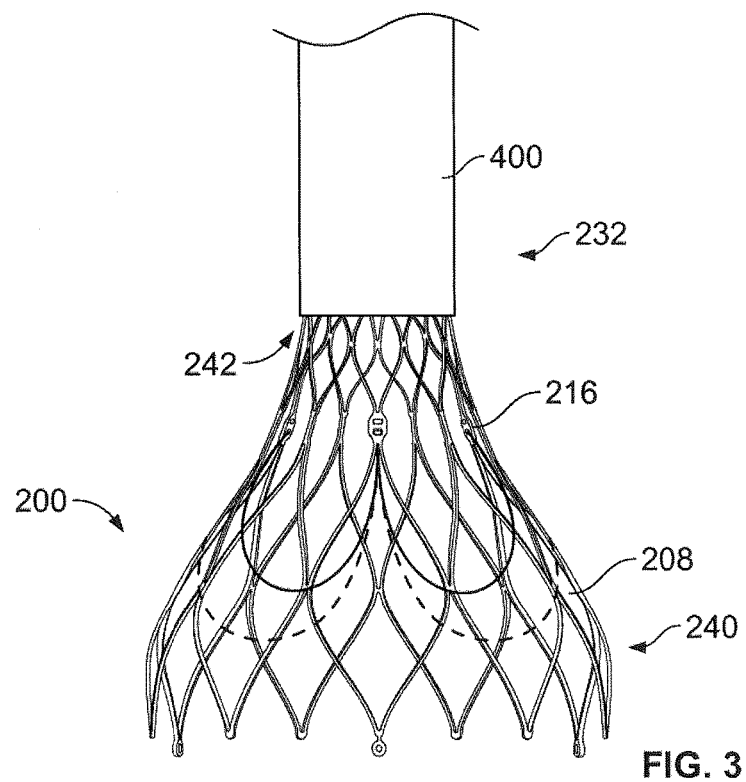
FIG. 3 is a fragmentary side elevational view showing partial deployment of a collapsible prosthetic heart valve using a transfemoral approach.

FIG. 3 illustrates transfemoral delivery of a prosthetic heart valve. In the transfemoral approach, the leading end of the delivery device points in the proximal direction of the heart. The valve is disposed in the delivery device with the annulus section toward the leading end of the delivery device. As seen in FIG. 3, using a transfemoral approach permits partial deployment of the annulus end 240 of the heart valve 200 by unsheathing it and allowing the valve to expand. For example, the sheath 400 of the delivery device may be retracted toward the trailing end of the delivery device while internal components of the delivery device (not shown) hold the valve in place. The distal end of the valve, including the aortic section, remains partially sheathed and coupled to the delivery device. The proximal end of the valve, including the annulus section 240 is forced to expand. It will be appreciated that the valve assembly 204, and specifically the function of leaflets 208, may be tested without fully deploying the heart valve 200, enabling a better assessment of the valve's functioning and final placement within the actual anatomy. Thus, if it appears that the valve needs to be moved, the heart valve 200 may be easily resheathed and repositioned. This concept is beneficial when dealing with less than ideal anatomical configurations.

In some circumstances, it may be desirable to use a transapical approach, shown as "B" in FIG. 2 as opposed to a transfemoral approach, shown as approach "A". For example, calcification in arteries may render tracking of a transfemoral approach difficult and make a transapical approach the more preferable route.

Figure 4A:
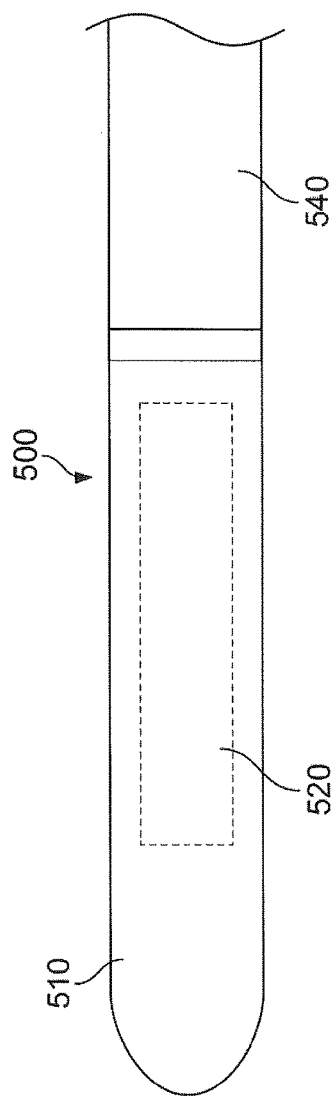
FIG. 4A is a fragmentary side elevational view of a conventional delivery device for use with a transapical approach.

FIG. 4A illustrates a conventional delivery device for use with a transapical approach. As seen in FIG. 4A, the transapical delivery device 500 includes a sheath 510 connected to a trailing end 540 via support core 530 (shown in FIG. 4B). Sheath 510 includes a compartment 520 for housing prosthetic heart valve 200.

Figure 4B:
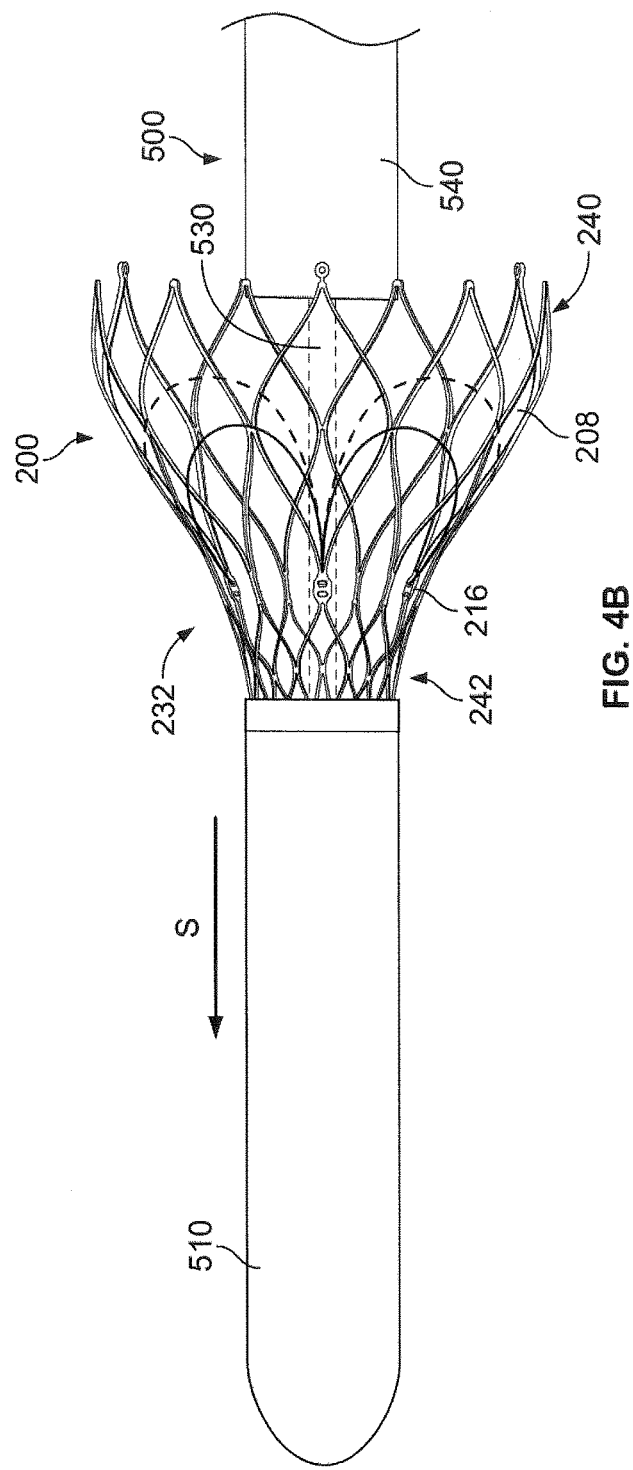
FIG. 4B is a fragmentary side elevational view of the delivery device of FIG. 4A showing partial deployment of a collapsible prosthetic heart valve using the transapical approach.

FIG. 4B illustrates partial deployment of a collapsible prosthetic heart valve 200 using the transapical approach. The deployment device is advanced in a forward direction through the apex of the heart and into the aorta until the annulus end 230 of the valve is disposed at or near the annulus of the native valve and sheath 510 projects through the native valve into the aorta. While the trailing end 540 is held in position, sheath 510 is translated away from the trailing end 540 in the forward direction of arrow "S" to remove prosthetic heart valve 200 from compartment 520 and release the prosthetic heart valve 200. In this configuration, the aortic section of the valve is near the leading end of the delivery device and the annulus section is near the trailing end. Thus, trailing-end-first deployment deploys the annulus section before the aortic section. The deployment process can be reversed before the sheath is fully deployed by reversing the movement of the sheath relative to the stent. In the conventional delivery system, when sheath 510 is advanced off the valve as illustrated by arrow "S," it moves in the distal direction relative to the patient and thus advances into the aortic arch 320 (FIG. 2). This may not be desirable if the patient has a diseased aortic arch. Moreover, because sheath 510 serves to house prosthetic heart valve 200, it typically has a large diameter. Thus, the possibility of trauma to the patient's heart exists when the large sheath 510 is advanced into the aortic arch 320 to deploy heart valve 200. If the prosthetic heart valve 200 is delivered transapically but released leading-end first as in the transfemoral approach, the result would be unsheathing of the aortic end of the heart valve 200 first, prohibiting the assessment of valve function before full release.

Thus, it would be desirable to deploy a prosthetic heart valve 200 aortic-end first while allowing the annulus end of the heart valve 200 to be fully expanded prior to being fully released from the delivery device so that the stent can be recaptured and repositioned after expansion of the annulus section. Moreover, it would be desirable to assess the function of such a valve and to then reposition or resheath the heart valve 200 as necessary without causing trauma by advancing a large sheath 510 into the aorta.

Figure 5A:
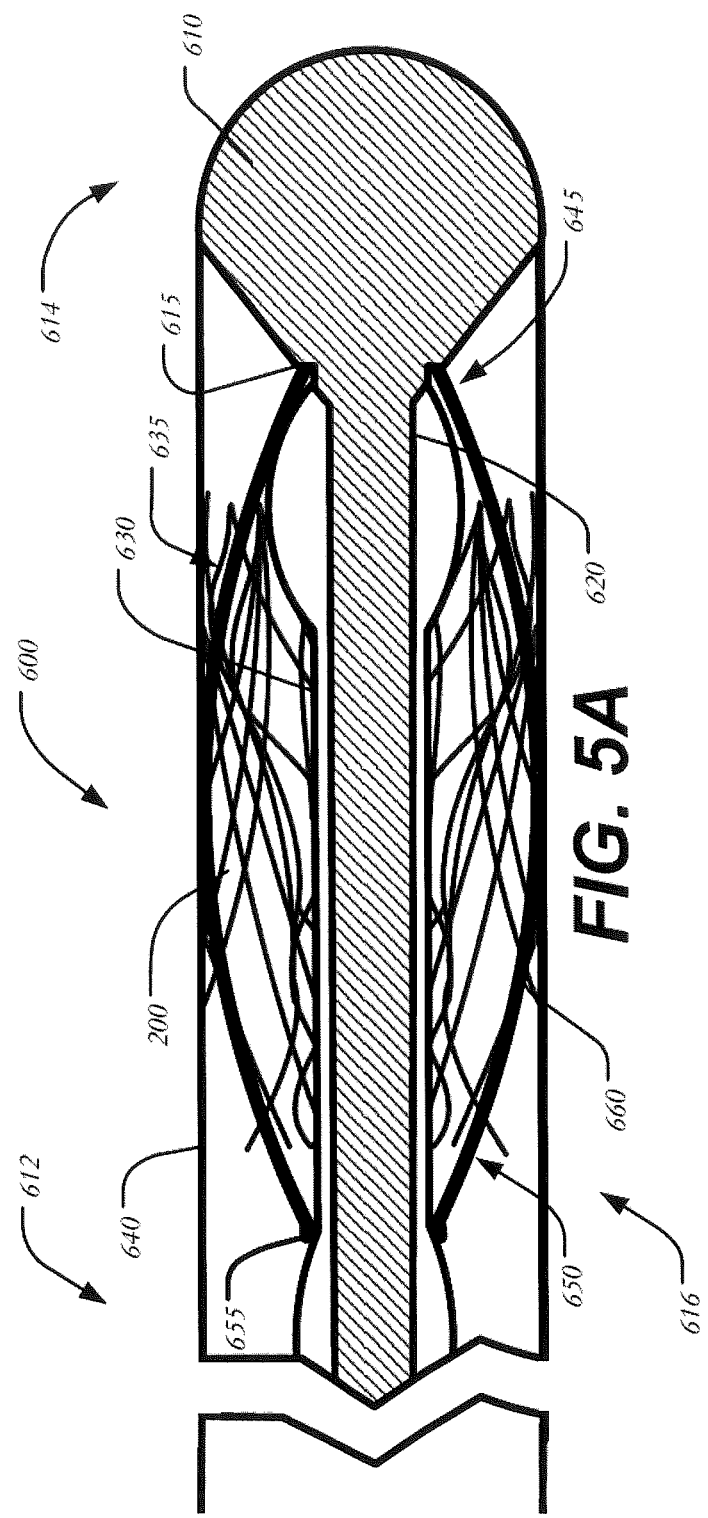
FIG. 5A is a fragmentary, diagrammatic cross-sectional view of a resheathable delivery device in a closed state for use with a transapical approach according to one embodiment of the present invention.

FIGS. 5A-D illustrate one embodiment of the present invention. This embodiment of a delivery device 600 has a trailing end 612, a leading end 614, and a catheter assembly 616 extending from the trailing end 612 to the leading end 614. The cross-sectional view of FIG. 5A illustrates the device in a fully closed state.

Delivery device 600 houses a collapsed prosthetic heart valve 200. For the sake of clarity, the prosthetic heart valve 200 is illustrated as a stent mesh without the valve portion. It will be understood, however, that the prosthetic heart valve 200 may be formed as a conventional heart valve 200 having a stent and a valve portion or configured as described above.

The catheter assembly 616 includes an inner core 620 extending from the trailing end 612 to the leading end 614, and an outer shaft 630 assembled over the inner core 620 and made slidable relative thereto. As shown in FIG. 5A, in the closed state of device 600, prosthetic heart valve 200 is disposed about outer shaft 630 near the leading end. Prosthetic heart valve 200 may be disposed about outer shaft 630 so that heart valve 200 translates with the outer shaft 630. A sheath 640 encloses the valve 200 within compartment 635, formed between the sheath 640 and the outer shaft 630. Sheath 640 may be formed as a cylinder or other hollow body having an open distal end 645. Sheath 640 may be independently slidable relative to both inner core 620 and outer shaft 630 such that sheath 640 is capable of being pulled back by the user to expose prosthetic heart valve 200.

A distal cap 610 may be connected to inner core 620 such that translation of inner core 620 actuates the distal cap 610. As seen in FIG. 5A, distal cap 610 may be configured as a partially hemispherical body shaped to mate with or abut open distal end 645 of sheath 640 to substantially cover open distal end 645 in the closed configuration. In at least some examples, distal cap 610 is blunt so as not to cause trauma to body tissue or organs during delivery or tracking through the vasculature. Moreover, as seen in FIG. 5A, because distal cap 610 does not itself house prosthetic heart valve 200, it may be made shorter and have a smaller diameter than sheath 510 of FIG. 4A so that it does not cause trauma. As will be described in more detail below, the distal cap 610 may be advanced a shorter distance into the aortic arch than sheath 510 of FIG. 4A to release valve 200.

A handle (not shown) for controlling deployment of a collapsible heart valve 200 located in the compartment 635 may be optionally coupled to the inner core 620, outer shaft 630 or sheath 640, such that the handle can provide a user maneuverability of the three elements. Such a handle may facilitate deployment of the device. In examples not including a handle, a user (e.g., a surgeon or an interventional cardiologist) may manually slide any of the inner core 620, outer shaft 630 or sheath 640 relative to any of the other two elements.

Delivery device 600 may include a retaining cage 650 disposed within sheath 640 for resheathing the prosthetic heart valve 200 during partial deployment. Retaining cage 650 may include a plurality of fingers 660. The trailing ends of the fingers 660 are connected to outer shaft 630 at junctions 655. Retaining cage 650 may include two, three, four, five, six or more individual fingers 660. Each of fingers 660 may be formed of strong but flexible material such as metal such as nitinol, a polymer or a woven material. In at least some examples, fingers 660 are formed of more than one material. Fingers 660 may be resilient or may be formed of a shape-memory material that allows fingers 660 to expand when released from within sheath 640. The structure and function of fingers 660 of retaining cage 650 will be more easily appreciated by examining the device in the partial deployed configuration as seen in FIG. 5B.

Fingers 660 are connected to outer shaft 630 at junctions 655 at their trailing ends. The fingers thus translate with outer shaft 630 when outer shaft 630 moves relative to sheath 640. Each junction 655 may be formed of a weld, adhesive or any other suitable method of coupling fingers 660 to outer shaft 630. Fingers 660 may also be interwoven with the annulus section of prosthetic heart valve 200. That is, in the collapsed condition depicted in FIG. 5A, the fingers may extend through some of the cells of the valve 200. The leading ends of fingers 660 may be adapted to couple to the distal cap 610 as will be described in more detail below. In the collapsed condition the leading ends of fingers are engaged with indentations 615 in cap 610.

In operation, the user may advance delivery device 600 in its closed configuration transapically through the apex of the left ventricle as illustrated by approach "B" in FIG. 2. Once inside the heart, the user may carefully advance the delivery device, including the inner core 620, the outer shaft 630 and the sheath 640, to the aortic valve at the target site of implantation by guiding the distal cap 610 to its intended position. The user may then retract sheath 640 by pulling it back toward the trailing end 612 while maintaining the position of inner core 620 and outer shaft 630, thereby exposing retaining cage 650 and heart valve 200.

FIG. 5B is a cross-sectional view of the delivery device 600 of FIG. 5A in a partially deployed state. In the partially deployed state, sheath 640 has been pulled back toward the trailing end of the device to expose prosthetic heart valve 200 and retaining cage 650. With the sheath 640 retracted, heart valve 200 and the retaining cage 650 expand. Fingers 660 of retaining cage 650 may remain interwoven with a portion of heart valve 200. Additionally, fingers 660 may remain coupled to distal cap 610 in this partially deployed configuration. In this example, the leading ends of the fingers are engaged with indentations 615 of cap 610. With the delivery device 600 partially deployed, fingers 660 are retained within indentations 615 and the retaining cage 650 remains intertwined with the heart valve 200.

With sheath 640 retracted, the self-expandable retaining cage 650 and heart valve 200 billow to their open configurations. The valve assembly engages the surrounding tissues. The user may then test the heart valve 200 for proper function. Though the retaining cage 650 remains interwoven with heart valve 200, it may be positioned in a manner so as not to impede the functioning of the heart valve 200. Heart valve 200 may be retrieved if necessary at this point. For example, if the positioning of the heart valve is found to be inaccurate, the fitment of the heart valve is poor, or if the heart valve is found to be defective, the user may retrieve or reposition the heart valve. This may be accomplished by sliding sheath 640 forward toward the leading end 614 over the inner core 620 and outer shaft 630. As the sheath 640 is advanced over outer shaft 630, the sheath 640 pushes against the fingers 660 of the retaining cage 650, forcing the retaining cage 650 to collapse and the heart valve 200 to collapse with it. The sheath 640 may be advanced until the delivery device 600 is in a substantially closed configuration as seen in FIG. 5A. The delivery device 600 may then be repositioned as desirable or completely removed from the patient if necessary.

Figure 5C:
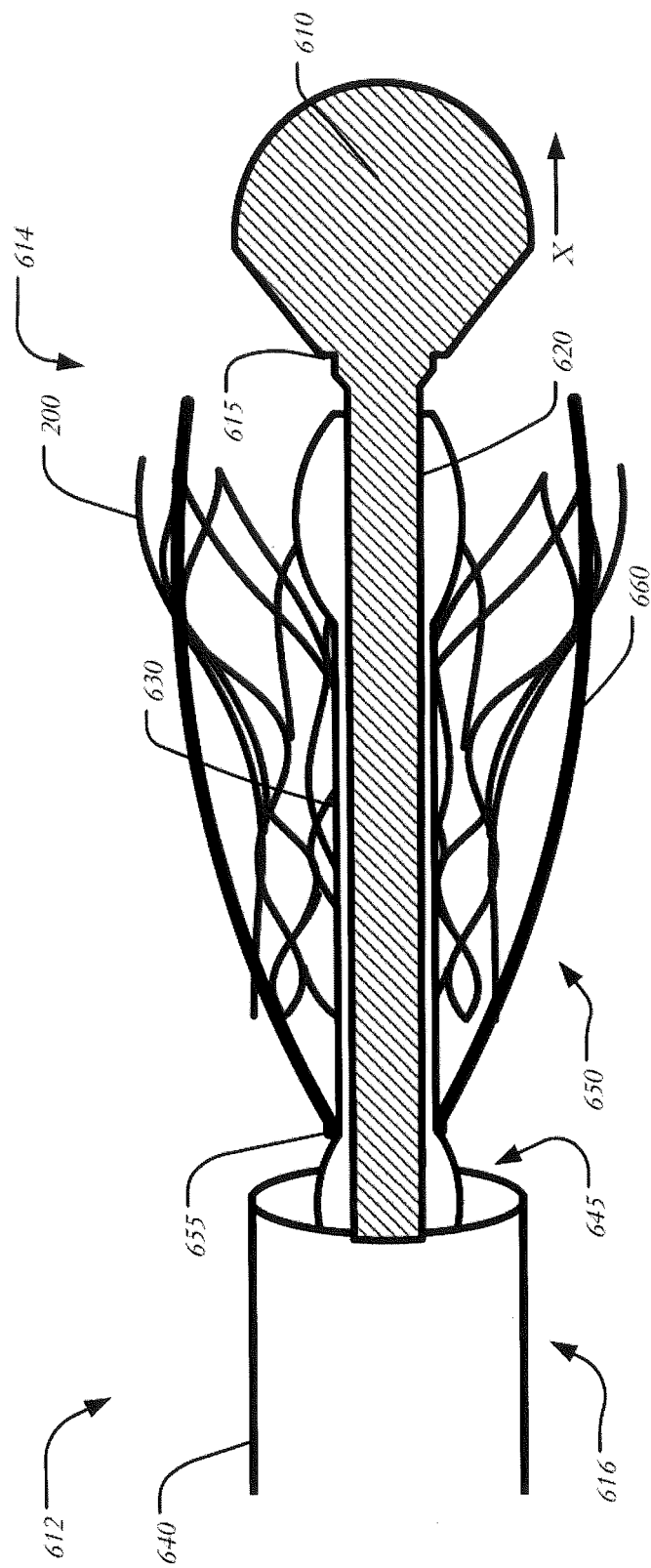
FIG. 5C is a cross-sectional view similar to FIGS. 5A and 5B of the delivery device of FIGS. 5A and 5B in a partial state of deployment.

If after testing the heart valve 200, the user is satisfied with the operation of the leaflets and the valve, the user may begin to remove the heart valve 200 from the delivery device 600. As seen in FIG. 5C, by advancing inner core 620 and thus the distal cap 610 forward slightly relative to outer shaft 630 as indicated by arrow "X", second ends of fingers 660 become released from indentations 615 of distal cap 610. Fingers 660 remain connected at their trailing ends at junctions 655 but are freed at their leading ends, permitting release of heart valve 200 from cage 650. Release from indentations 615 may cause biased fingers 660 to be disposed substantially parallel to outer shaft 630 at their leading ends. The slight movement of cap 610 does not cause the cap to impinge on the aorta.

Figure 5D:
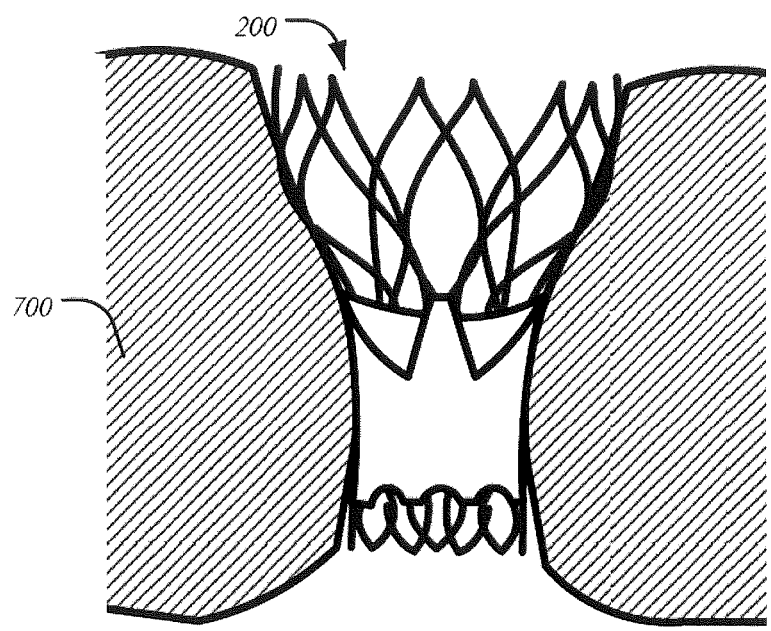
FIG. 5D is a view similar to FIGS. 5A-C depicting removal of the delivery device of FIGS. 5A-C after the implantation of the valve.
Figure 5D:
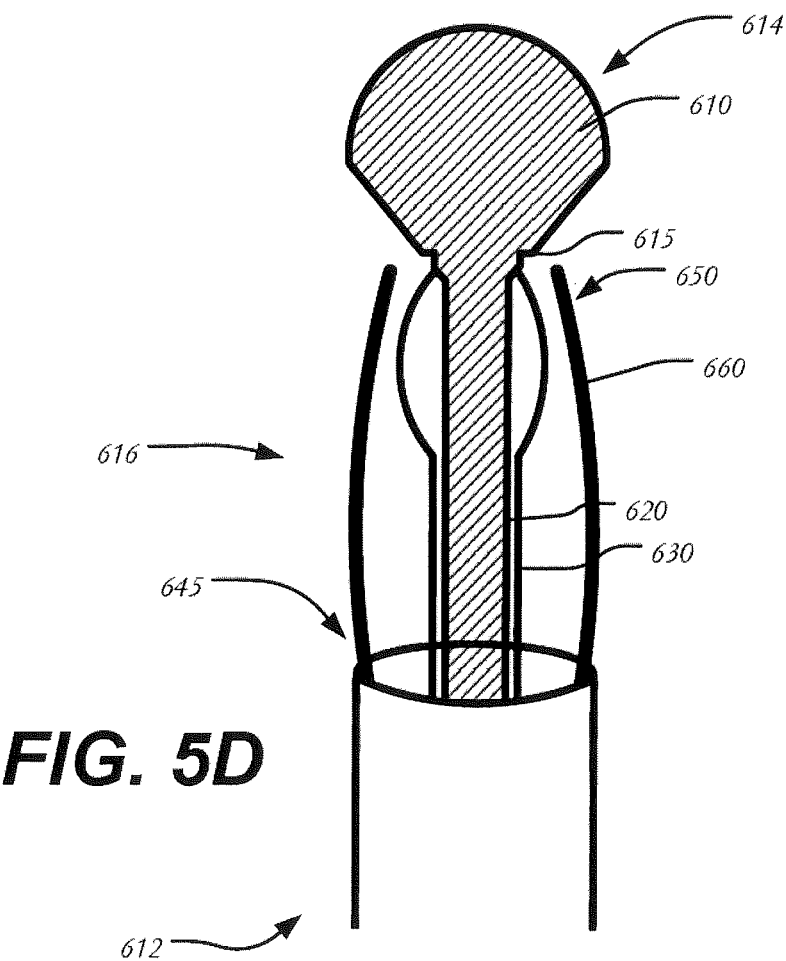

Once the fingers are in this released condition, delivery device 600 may be removed from the patient by first pulling it back toward trailing end 612. Because fingers 660 are free at their leading ends, heart valve 200 becomes untwined from retaining cage 650. The tissue engaged with the valve holds the valve in place during this process. Heart valve 200 may then slide over outer shaft 630 and distal cap 610 as delivery device 600 is retracted. As seen in FIG. 5D, the increasing diameter of distal cap 610 from the trailing end 612 to the leading end 614 may facilitate movement of heart valve 200 over distal cap 610. Once heart valve 200 has been freed completely from the delivery device, delivery device 600 may be removed from the patient.

Although the invention herein has been described with reference to particular embodiments, it is to be understood that these embodiments are merely illustrative of the principles and applications of the present invention. For example, although the invention is described herein as applied to a prosthetic heart valve for replacing a native aortic valve, the invention is not so limited, and may be applied to prosthetic valves for replacing other types of cardiac valves. It will also be noted that while the inventions herein have been described predominately in terms of a tricuspid valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Moreover, the delivery device can be used to place stents without valves. In these various applications, either the proximal or distal end of the device to be implanted can be disposed toward the leading end of the delivery device. It is therefore to be understood that numerous modifications may be made to the illustrative embodiments and that other arrangements may be devised without departing from the spirit and scope of the present invention as defined by the appended claims. For example, instead of indentations, the distal ends of fingers 760 may be releasably coupled to the distal cap via any other suitable method of attachment.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A medical device implantation system comprising:
   (a) a shaft extending in longitudinal directions;
   (b) a medical device including a self-expanding stent disposed over an outer surface of the shaft and surrounding the shaft, the stent being expandable in radially outward directions transverse to the longitudinal directions;
   (c) a sheath surrounding the shaft, the sheath being slidable relative to the shaft in a first longitudinal direction from a closed position in which the sheath surrounds the stent to an open position in which the sheath is longitudinally offset from the stent and in a second longitudinal direction from the open position towards the closed position;
   (d) a cage including a plurality of fingers, each finger having a first end attached to the shaft and extending in the second longitudinal direction from the first end to a second end, each finger having an engagement section extending radially outwardly of the stent over at least a portion of the stent adjacent the first end of the finger when the stent is in a collapsed condition, the engagement section of each finger being movable away from the shaft during expansion of the stent and being movable toward the shaft responsive to movement of the sheath relative to the shaft in the second longitudinal direction so that the stent can be collapsed by moving the sheath in the second longitudinal direction;
   (e) a distal cap slidable relative to the shaft and having indentations for receiving the second ends of the plurality of fingers; and
   (f) an inner core disposed within the shaft and translatable relative thereto, the distal cap being coupled to the inner core, the inner core being movable from an initial position at which the distal cap directly abuts a free end of the shaft and the second ends of the plurality of fingers are received in the indentations of the distal cap, to a release position at which the distal cap is spaced from the free end of the shaft and the second ends of the plurality of fingers are withdrawn from the indentations,
   wherein in an intermediate configuration of the system, the sheath is in the open position, the distal cap directly abuts the free end of the shaft, the first ends of the plurality of fingers are attached to the shaft, the second ends of the plurality of fingers are received in the indentations of the distal cap, and the stent is in an expanded condition.

2. A system as claimed in claim 1 wherein the shaft has a trailing end and a leading end, the first longitudinal direction is a rearward direction toward the trailing end of the shaft, and the second longitudinal direction is a forward direction toward the leading end of the shaft.

3. A system as claimed in claim 2 wherein the second ends are remote from the first ends and wherein the second ends of the plurality of fingers are free from the shaft when the stent is in a fully-expanded condition so that when the stent is in the fully-expanded condition and engaged with the body of a subject, the plurality of fingers can be disengaged from the stent by retracting the shaft rearwardly relative the body of the subject.

4. A system as claimed in claim 1 wherein the plurality of fingers are formed of a shape-memory alloy capable of expanding when the sheath is retracted.

5. A system as claimed in claim 4 wherein the plurality of fingers are formed of nitinol.

6. A system as claimed in claim 1 wherein the plurality of fingers are interwoven with the stent when the sheath is in the open position.

7. A system as claimed in claim 1 further comprising a handle coupled to the shaft and the sheath, the handle being capable of actuating the shaft and the sheath independently.

8. A system as claimed in claim 1 wherein the medical device is a prosthetic heart valve.

9. A system as claimed in claim 1 wherein the system is sized for transapical delivery.

10. The system as claimed in claim 1 wherein the distal cap in the initial position encloses an open end of the sheath.

11. A medical device implantation system comprising:
    (a) a shaft extending in longitudinal directions;
    (b) a medical device including a self-expanding stent disposed over an outer surface of the shaft and surrounding the shaft, the stent being expandable in radially outward directions transverse to the longitudinal directions;
    (c) a sheath surrounding the shaft, the sheath being slidable relative to the shaft in a first longitudinal direction from a closed position in which the sheath surrounds the stent to an open position in which the sheath is longitudinally offset from the stent and in a second longitudinal direction from the open position towards the closed position;
    (d) a retaining cage coupled to the shaft, the retaining cage being configured and arranged to collapse the stent by moving the sheath relative to the shaft in the second longitudinal direction from the open position to the closed position, the retaining cage including a plurality of fingers, each finger having a first end attached to the shaft and extending in the second longitudinal direction from the first end to a second end;
    (e) an inner core disposed within the shaft and translatable relative thereto; and
    (f) a distal cap having indentations for receiving the second ends of the plurality of fingers, the distal cap being coupled to the inner core, the inner core being movable from an initial position at which the distal cap directly abuts a free end of the shaft and the second ends of the plurality of fingers are received in the indentations of the distal cap, to a release position at which the distal cap is spaced from the free end of the shaft and the second ends of the plurality of fingers are withdrawn from the indentations,
    wherein in an intermediate configuration of the system, the sheath is in the open position, the distal cap directly abuts the free end of the shaft, the first ends of the plurality of fingers are attached to the shaft, the second ends of the plurality of fingers are received in the indentations of the distal cap, and the stent is in an expanded condition.

12. A system as claimed in claim 11 wherein the shaft has a trailing end and a leading end, the first longitudinal direction is a rearward direction toward the trailing end of the shaft, and the second longitudinal direction is a forward direction toward the leading end of the shaft.

13. A system as claimed in claim 11 wherein the system is sized for transapical delivery of a heart valve.

14. A method of delivering an implantable medical device, comprising:
   (a) advancing a delivery system to a target location in the body of a subject, the delivery system including a delivery apparatus having (i) a shaft extending in first and second longitudinal directions, (ii) a medical device including a self-expanding stent in a collapsed condition surrounding the shaft, (iii) a cage including longitudinally-extending fingers having first ends attached to the shaft, engagement sections disposed outwardly of the stent, and second ends, (iv) a sheath in a closed position in which the sheath surrounds the stent and the fingers, (v) an inner core disposed within the shaft and translatable relative thereto, and (vi) a cap coupled to the inner core, the cap having a plurality of indentations and the second ends of the fingers being disposed in the indentations of the cap when the inner core is in an initial position at which the cap directly abuts a free end of the shaft;
   (b) moving the sheath relative to the shaft in the first longitudinal direction from the closed position to an open position in which the sheath is longitudinally offset from the stent; and
   (c) expanding the stent until the stent is at least partially engaged with the body of the subject when the distal cap directly abuts the free end of the shaft, the first ends of the fingers are attached to the shaft and the second ends of the fingers are received in the indentations of the distal; the engagement sections of the fingers are displaced radially outwardly by the expanding of the stent; and
   (d) moving the inner core to a release position at which the cap is spaced from the free end of the shaft and the second ends of the fingers are withdrawn from the indentations of the cap; and
   (e) releasing the medical device from the cage and withdrawing the delivery apparatus from the body of the subject,
   wherein the step of expanding the stent occurs before the step of moving the inner core.

15. The method of claim 14, further comprising evaluating positioning or functionality of the medical device after the expanding the stent step and prior to releasing the medical device from the cage.

16. The method of claim 15 further comprising a step of displacing the engagement sections of the fingers radially inwardly to at least partially collapse the stent.

17. The method of claim 16 wherein the step of displacing the engagement sections of the fingers radially inwardly includes moving the sheath relative to the shaft in the second longitudinal direction.

18. The method of claim 16, wherein, prior to the expanding the stent step, the fingers have sections extending through openings in the stent and the step of releasing the medical device from the cage includes untwining the fingers from the stent.

19. The method of claim 14, wherein the step of releasing the medical device from the cage comprises moving the shaft and the fingers in the first longitudinal direction relative to the body of the subject.

20. The method of claim 14, wherein the medical device is a prosthetic aortic valve and the target location is at or adjacent the native aortic valve.

21. The method of claim 20 wherein the advancing step includes advancing the delivery system through the left ventricle to the target location, and wherein the step of moving the sheath relative to the shaft in the first longitudinal direction includes moving the sheath from the target location toward the left ventricle.

* * * * *